United States Patent
Hayashi

(10) Patent No.: US 8,622,547 B2
(45) Date of Patent: Jan. 7, 2014

(54) FUNDUS OBSERVATION APPARATUS

(75) Inventor: Takefumi Hayashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 100 days.

(21) Appl. No.: 13/266,148

(22) PCT Filed: Apr. 2, 2010

(86) PCT No.: PCT/JP2010/002428
§ 371 (c)(1),
(2), (4) Date: Oct. 25, 2011

(87) PCT Pub. No.: WO2010/125746
PCT Pub. Date: Nov. 4, 2010

(65) Prior Publication Data
US 2012/0044456 A1    Feb. 23, 2012

(30) Foreign Application Priority Data
Apr. 30, 2009    (JP) .................................. 2009-110840

(51) Int. Cl.
*A61B 3/14*    (2006.01)
*A61B 3/12*    (2006.01)

(52) U.S. Cl.
CPC   *A61B 3/1225* (2013.01); *A61B 3/14* (2013.01)
USPC ........................................................ 351/206

(58) Field of Classification Search
USPC ................................................. 351/206, 208
See application file for complete search history.

(56) References Cited

U.S. PATENT DOCUMENTS

| | | | |
|---|---|---|---|
| 6,377,349 B1 | 4/2002 | Fercher | |
| 2005/0018132 A1 | 1/2005 | Fukuma et al. | |
| 2006/0100528 A1 | 5/2006 | Chan et al. | |
| 2007/0222945 A1* | 9/2007 | Tsukada et al. | 351/205 |
| 2007/0236661 A1* | 10/2007 | Fukuma et al. | 351/205 |
| 2009/0033870 A1* | 2/2009 | Hangai et al. | 351/206 |

FOREIGN PATENT DOCUMENTS

| | | |
|---|---|---|
| EP | 1908397 A2 | 4/2008 |
| JP | 09-276232 A | 10/1997 |
| JP | 11-325849 A | 11/1999 |

(Continued)

OTHER PUBLICATIONS

Extended European Search Report for 10769448.1-1657/2425763 dated Feb. 27, 2013.

(Continued)

*Primary Examiner* — Ricky Mack
*Assistant Examiner* — William Alexander
(74) *Attorney, Agent, or Firm* — Pearne & Gordon LLP

(57) ABSTRACT

The controller 210 changes the projection region of the Landolt ring T on the fundus Ef by changing, based on the scanning region R, the relative display position of the Landolt ring T and the fixation target V on the LCD 39, thereby overlapping the scanning region R and the projection region each other. Under this condition, the fundus observation apparatus 1 executes the eyesight measurement and OCT measurement, obtains the eyesight value at the site of interest of the fundus Ef, and forms a tomographic image of the fundus Ef in the scanning region R. The controller 210 stores in the storage 212 the eyesight value at the site of interest and the tomographic image corresponding to the scanning line closest to the measurement position of eyesight while correlating them with each other, and allows them to be displayed on the display device 3.

10 Claims, 8 Drawing Sheets

(56) References Cited

FOREIGN PATENT DOCUMENTS

| | | |
|---|---|---|
| JP | 2002-139421 A | 5/2002 |
| JP | 2002-209849 A | 7/2002 |
| JP | 2006-153838 A | 6/2006 |
| JP | 2007-24677 A | 2/2007 |
| JP | 2008-073099 A | 4/2008 |
| JP | 2008-148930 A | 7/2008 |
| WO | 2003-041571 A1 | 5/2003 |
| WO | 2009059400 A1 | 5/2009 |

OTHER PUBLICATIONS

International Search Report for PCT/JP2010/002428; Jun. 22, 2010.

* cited by examiner

FUNDUS OBSERVATION APPARATUS

TECHNICAL FIELD

The present invention relates to a fundus observation apparatus configured to form images of a fundus of an eye by using optical coherence tomography.

BACKGROUND ART

In recent years, optical coherence tomography that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field.

Patent Document 1 discloses a device to which optical coherence tomography is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Patent Document 1 uses a technique of so-called "Fourier Domain OCT (Optical Coherence Tomography)." That is to say, the device irradiates a low coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the device described in Patent Document 1 is provided with a Galvano mirror that scans with a light beam (a signal light), and is thereby configured to form an image of a desired measurement target region of the object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction (x-direction) and the vertical direction (y-direction) to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Patent Documents 3 and 4 disclose other types of OCT devices. Patent Document 3 describes an OCT device that images the morphology of an object by sweeping the wavelength of light that is irradiated to an object, acquiring the spectral intensity distribution based on an interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses a configuration in which the OCT is applied to the ophthalmologic field. Before the OCT device was applied to the ophthalmologic field, a fundus observation apparatus such as a retinal camera had been used (for example, refer to Patent Document 6).

Compared to a retinal camera that can only photograph a fundus from the front, a fundus observation apparatus using OCT has a merit that tomographic images and 3-dimensional images of a fundus are obtained. Therefore, contribution to increase of the diagnosis accuracy and early detection of a lesion are expected.

The fundus observation apparatus using optical coherence tomography thus occupies an important place in diagnosis and treatment of diseases. However, in reality, eyesight values are currently used in order to determine the necessity of treatment and the presence or absence of its effect.

This is due to the fact that the main purpose of treatment is the improvement of eyesight, and the change in the morphology of the fundus (for example, hole shrinkage due to treatment of the macular hole) can be confirmed by the fundus observation apparatus, but it cannot be determined whether or not the change in the morphology results in improvement of eyesight without relying on eyesight measurement.

It should be noted that eyesight measurement is an eye examination in which a visual target for measuring eyesight such as a Landolt ring is presented to the subject, commonly carried out using a subjective optometer (see, for example, Patent Document 7).

PRIOR ART DOCUMENTS

Patent Documents

[Patent Document 1]
  Japanese Unexamined Patent Application Publication No. Hei 11-325849
[Patent Document 2]
  Japanese Unexamined Patent Application Publication No. 2002-139421
[Patent Document 3]
  Japanese Unexamined Patent Application Publication No. 2007-24677
[Patent Document 4]
  Japanese Unexamined Patent Application Publication No. 2006-153838
[Patent Document 5]
  Japanese Unexamined Patent Application Publication No. 2008-73099
[Patent Document 6]
  Japanese Unexamined Patent Application Publication No. Hei 9-276232
[Patent Document 7]
  Japanese Unexamined Patent Application Publication No. 2008-148930

DISCLOSURE OF THE INVENTION

Problem that the Invention is to Solve

However, with eyesight measurement, it cannot be determined which site of the fundus is used to see the target (i.e., it cannot be determined which site of the fundus is projected with the target), and it cannot be determined if the eyesight value of the treatment sight has actually improved. For example, in a healthy eye, the target is projected on the macula flava due to the target being recognized in the macula flava having the highest visual ability; however, when there is a disorder in the macula flava, the target tends to be captured by a site other than the macula flava, so the eyesight value of the affected site actually cannot always be measured. In such a case, it is preferable that the visual ability be able to be confirmed by conducting eyesight measurement at the site of interest (treatment site, diagnosed site, etc.) of the fundus, while being able to confirm the morphology of the fundus by obtaining an image of the site of interest. However, conventional devices have not been able to obtain an image of the eyesight measurement position. Consequently, for example, it has not been possible to determine whether or not the treatment is actually reflected in improvement of eyesight.

Moreover, the viewing angle (size) of the visual target for measuring eyesight projected on the fundus is sometimes changed due to the refractive power (eye refractive power) of the eye, and there has been a problem in that the eyesight value cannot be precisely measured in such a case.

Furthermore, it is also conceivable that a conventional fundus observation apparatus is added with a target presenting function, but in such a case the subject has to simultaneously visually confirm the signal light, the fixation target and the visual target for measuring eyesight, increasing the complexity of the examination and possibly causing adverse effects.

This invention resolves the above-mentioned problem, with the purpose of providing a fundus observation apparatus capable of obtaining an image at the eyesight measurement site of the fundus.

Means for Solving the Problem

In order to achieve the aforementioned objects, an invention according to claim 1 is a fundus observation apparatus comprising: a projection part that includes a display part to display a visual target for measuring eyesight, and projects, via a predetermined optical path, said displayed visual target for measuring eyesight to the fundus of an eye; a light source that outputs low-coherence light; an optical system that splits said output low-coherence light into signal light and reference light, generates interference light by superposing said signal light that has passed through said fundus via said predetermined optical path and said reference light that has passed through a reference optical path, and detects said interference light; a scanning part that scans said fundus with said signal light; a controlling part that overlaps the projection region of said visual target for measuring eyesight projected by said projection part and the scanning region of said signal light scanned by said scanning part each other; an image forming part that forms an image of said fundus based on the detection results of interference light generated by superposing said signal light with which said scanning region is scanned and said reference light; and a storage part that stores said formed image and an eyesight value measured using said visual target for measuring eyesight while correlating them with each other.

Further, an invention according to claim 2 is the fundus observation apparatus according to Claim 1, wherein said controlling part controls said projection part based on the scanning region of said signal light scanned by said scanning part to overlap the projection region of said visual target for measuring eyesight in said fundus on the scanning region of said signal light.

Further, an invention according to claim 3 is the fundus observation apparatus according to Claim 2, wherein: said display part displays a fixation target for fixing said eye along with said visual target for measuring eyesight; said projection part projects said displayed fixation target on said fundus along with said visual target for measuring eyesight; and said controlling part changes said projection region by changing, based on said scanning region, the relative display positions of said visual target for measuring eyesight and said fixation target displayed by said display part.

Further, an invention according to claim 4 is the fundus observation apparatus according to Claim 1, wherein said controlling part controls said scanning part based on the display position of said visual target for measuring eyesight displayed by said display part to overlap the scanning region of said signal light in said fundus on the projection region of said visual target for measuring eyesight.

Further, an invention according to claim 5 is the fundus observation apparatus according to Claim 1, wherein said controlling part allows said visual target for measuring eyesight corresponding to different eyesight values to be projected on said fundus, by allowing said visual target for measuring eyesight of different sizes to be displayed on said display part to change the size of said projection region.

Further, an invention according to claim 6 is the fundus observation apparatus according to Claim 5, wherein: said predetermined optical path is provided with a focusing lens that moves along an optical axis thereof to change the focus position of light towards said fundus; and said controlling part adjusts the size of said visual target for measuring eyesight displayed on said display part based on the position of said focusing lens.

Further, an invention according to claim 7 is the fundus observation apparatus according to Claim 5, further comprising an operation part for inputting response contents for said visual target for measuring eyesight projected on said fundus, wherein said controlling part changes the size of said visual target for measuring eyesight displayed on said display part based on said input response contents, and determines the eyesight value of said eye based on said response contents according to this change.

Further, an invention according to claim 8 is the fundus observation apparatus according to Claim 1, further comprising an operation part for inputting response contents for said visual target for measuring eyesight projected on said fundus, wherein said controlling part controls said projection part to project said visual target for measuring eyesight corresponding to a predetermined eyesight value to said fundus, determines whether said input response contents for this visual target for measuring eyesight are true or false, and if it is determined that they are correct, then controls said scanning part to scan said scanning region overlapping the projection region with said signal light.

Further, an invention according to claim 9 is the fundus observation apparatus according to Claim 1, wherein said light source outputs invisible light as said low-coherence light.

Further, an invention according to claim 10 is the fundus observation apparatus according to Claim 9, wherein said light source outputs near-infrared light of center wavelength within the range substantially from 1050 to 1060 nm.

Effect of the Invention

According to the fundus observation apparatus related to the present invention, an image of the scanning region of the signal light on the fundus can be formed with said scanning region being superposed on the projection region of the visual target for measuring eyesight, and it is possible to measure the eyesight in the projection region and then store the formed image and the measured eyesight value while associating them with each other, allowing an image of the eyesight measurement site of the fundus to be obtained.

MODE FOR CARRYING OUT THE INVENTION

An example of an embodiment of a fundus observation apparatus according to the present invention will be described in detail with reference to the drawings.

The fundus observation apparatus according to the present invention forms tomographic images of a fundus using optical coherence tomography. Optical coherence tomography of an arbitrary type involving scanning with a signal light such as a Fourier Domain type, a swept source type, etc. are applicable to the fundus observation apparatus. It should be noted that an image obtained by optical coherence tomography is sometimes referred to as an OCT image. Furthermore, a measuring action for forming an OCT image is sometimes referred to as an OCT measurement.

In the following embodiments, a configuration to which a Fourier-Domain-type is applied will be described in detail. To be specific, in these embodiments, similar to a device disclosed in Patent Document 5, a fundus observation apparatus that is capable of obtaining both tomographic images and photographed image of a fundus will be picked up.

[Configuration]

Figure 1:
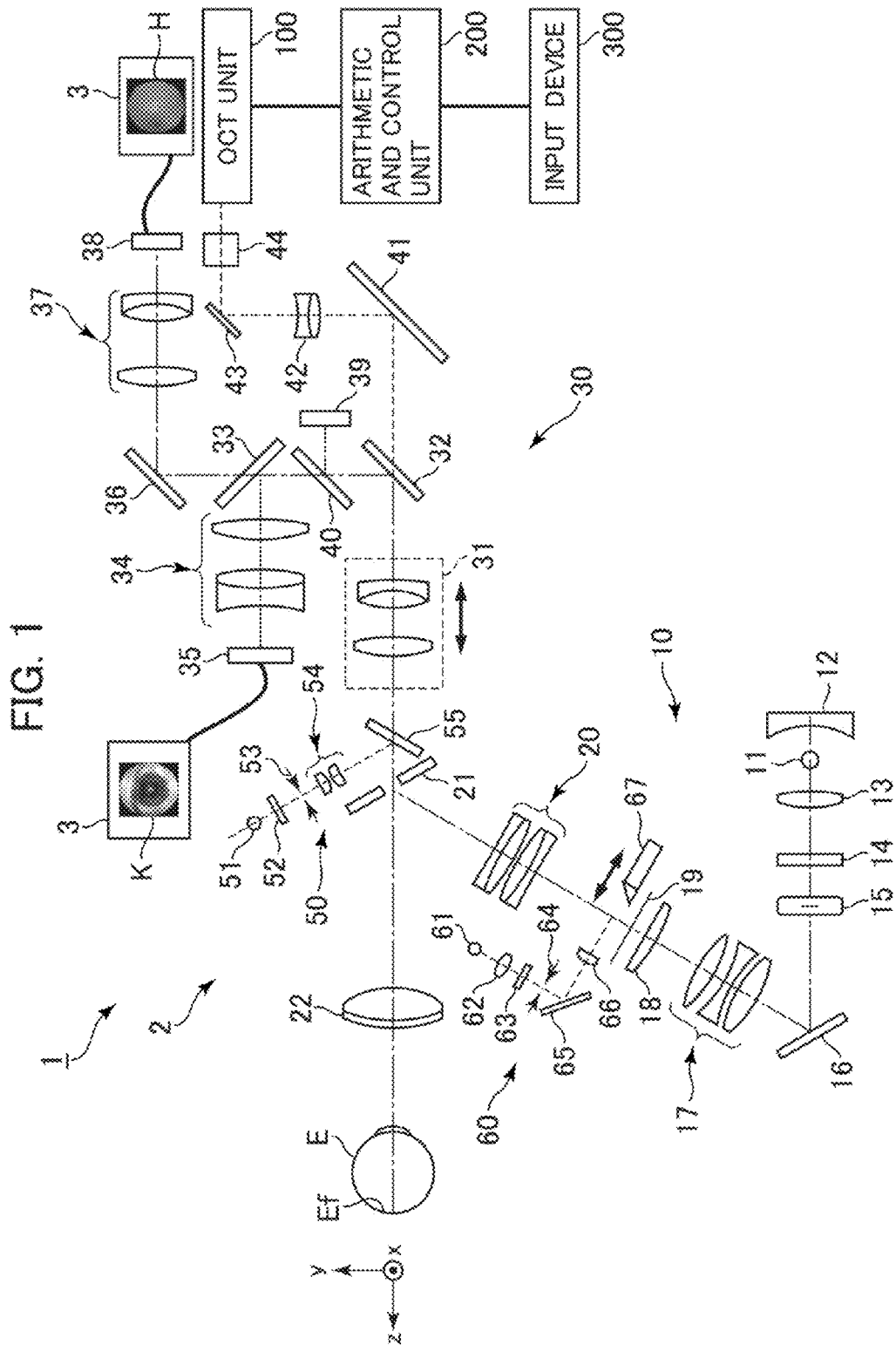
FIG. 1 is a schematic view showing an example of a configuration of an embodiment of a fundus observation apparatus according to the present invention.
Figure 2:
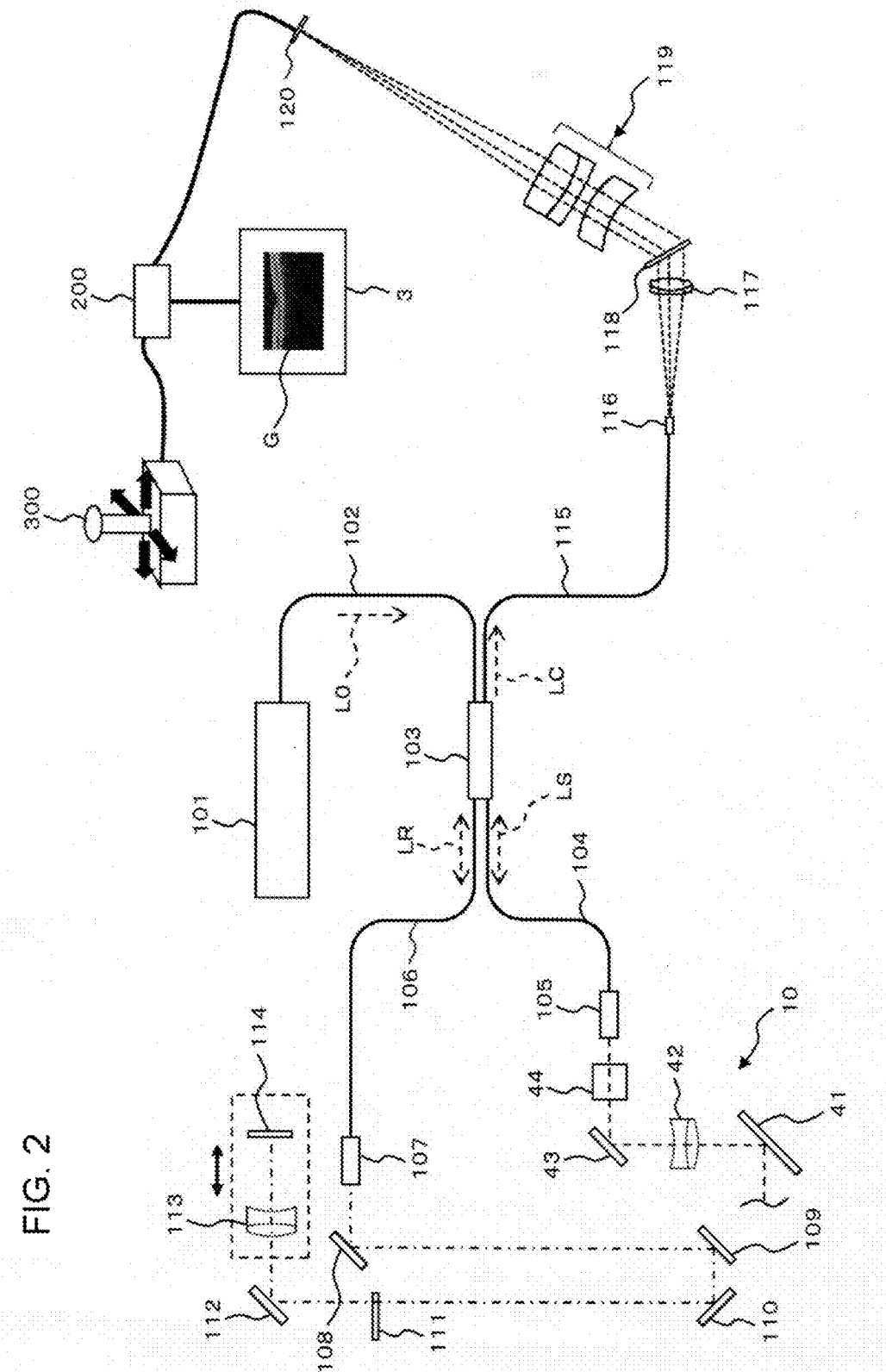
FIG. 2 is a schematic view showing an example of a configuration of an embodiment of a fundus observation apparatus according to the present invention.

A fundus observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit shown in FIG. 1 is provided with an optical system for forming a 2-dimensional image (fundus image) representing the surface morphology of the fundus Ef of an eye E. Fundus images include observation images, photographed images, etc. The observation image is, for example, a monochrome image formed at a prescribed frame rate using near-infrared light. The photographed image is, for example, a color image captured by flashing visible light. It should be noted that the retinal camera unit 2 may also be configured so as to be capable of capturing other types of images such as a fluorescein angiography image or an indocyanine green fluorescent image.

The retinal camera unit 2 is provided with a chin rest and a forehead placement for retaining the face of the subject, similar to a conventional retinal camera. Moreover, like a conventional retinal camera, the retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors 35, 38). Moreover, the imaging optical system 30 guides a signal light LS coming from the OCT unit 100 to the fundus Ef, and guides the signal light propagated through the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focusing lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image) K based on the fundus reflection light detected by the CCD image sensor 35 is displayed on a display device 3.

The imaging light source 15 consists of, for example, a xenon lamp. The light (imaging illumination light) output from the imaging light source 15 is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (photographed image) H based on the fundus reflection light detected by the CCD image sensor 38 is displayed on the display device 3. It should be noted that the display device 3 for displaying an observation image K and the display device 3 for displaying a photographed image H may be the same or different.

An LCD (Liquid Crystal Display) 39 displays a fixation target or a visual target for measuring eyesight. The fixation target is a visual target for fixing the eye E, and is used when photographing a fundus or forming a tomographic image. The visual target for measuring eyesight is a visual target used for measuring an eyesight value of the eye E, for example, such as Landolt rings. It should be noted that the visual target for measuring eyesight is sometimes simply referred to as a target.

Part of the light output from the LCD 39 is reflected by a half-mirror 40, reflected by the dichroic mirror 32, passes through the aperture part of the aperture mirror 21 via the focusing lens 31 as well as a dichroic mirror 55, is refracted by the object lens 22 and projected to the fundus Ef. LCD 39 is an example of a "display part" of the invention. Moreover, LCD 39 and the above-mentioned group of optical elements that project light output from LCD 39 on the fundus Ef are a "projection part" of the invention.

By changing a display position of the fixation target on the screen of the LCD 140, it is possible to change a fixation position of the eye E. As the fixation position of the eye E, there are a position for acquiring an image centered on the macula of the fundus Ef, a position for acquiring an image centered on the optic papilla, a position for acquiring an image centered on the fundus center between the macula and the optic papilla, and so on, for example, as in conventional retinal cameras.

Furthermore, as with conventional fundus cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from the LED (Light Emitting Diode) 51 of the alignment optical system 50 is reflected by the dichroic mirror 55 via diaphragms 52, 53 and a relay lens 54, passes through the aperture part of the aperture mirror 21, and is projected onto the cornea of the eye E by the object lens 22.

Part of cornea reflection light of the alignment light is transmitted through the dichroic mirror 55 via the object lens 22 and the aperture part, passes through the focusing lens 31, is reflected by the dichroic mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 along with the observation image K. A user conducts alignment by an operation that is the same as conventional fundus cameras. It should be noted that alignment may be performed, by an arithmetic and control unit 200, as a result of analyzing the position of the alignment target and moving the optical system.

In order to conduct focus adjustment, the reflection surface of a reflection rod 67 is provided in a slanted position on the light path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light (split target) captured by the CCD image sensor 35 is displayed on the display device 3 along with an observation image K. The arithmetic and control unit 200, as in the past, analyzes the position of the split target, and moves the focusing lens 31 and the focus optical system 60 for focusing. It should be noted that focusing may be performed manually while visually recognizing the split target.

An optical path including a mirror 41, collimator lens 42, and Galvano mirrors 43, 44 is provided behind the dichroic mirror 32. The optical path is connected to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44.

[OCT Unit]

The OCT unit 100 shown in FIG. 2 is provided with an optical system for obtaining a tomographic image of the fundus Ef. The optical system has a similar configuration to a conventional Fourier-Domain-type OCT device. That is to say, the optical system is configured to split a low coherence light into a reference light and a signal light, make the signal light propagated through a fundus and the reference light propagated through a reference optical path interfere with each other to generate an interference light, and detects the spectral components of this interference light. This detection result (detection signal) is transmitted to the arithmetic and control unit 200.

A light source unit 101 outputs a low coherence light L0. The low coherence light L0 is, for example, light (invisible light) consisting of wavelengths that is impossible to be detected by human eyes. Furthermore, the low coherence light L0 is, for example, near-infrared light having the center wavelength of about 1050-1060 nm. The light source unit 101 is configured to include light output device, such as an SLD (super luminescent diode), SOA (Semiconductor Optical Amplifier) and the like. A light source unit 101 is an example of a "light source" of the invention.

The low coherence light L0 output from the light source unit 101 is guided to a fiber coupler 103 by an optical fiber 102 and split into signal light LS and reference light LR. It should be noted that the fiber coupler 103 acts both as a means to split light (splitter) as well as a means to synthesize light (coupler), but herein the same is conventionally referred to as a "fiber coupler."

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103.

The reference light LR is guided by an optical fiber 106 and becomes a parallel light flux by a collimator lens unit 107.

Furthermore, the reference light LR is reflected by mirrors 108, 109, 110, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element for dispersion compensation (pair prism, etc.) and/or an optical element for polarization correction (wave plate, etc.) may also be provided for the optical path (reference optical path) of the reference light LR.

The fiber coupler 103 superposes the fundus reflection light of the signal light LS and the reference light LR reflected by the reference mirror 114. Interference light LC thus generated is guided by an optical fiber 115 and output from an exit end 116. Furthermore, the interference light LC is converted to a parallel light flux by a collimator lens 117, spectrally divided (spectrally decomposed) by a diffraction grating 118, converged by the convergence lens 119, and projected onto the light receiving surface of a CCD image sensor 120.

The CCD image sensor 120 is for example a line sensor, and detects the respective spectral components of the spectrally decomposed interference light LC and converts the components into electric charges. The CCD image sensor 120 accumulates these electric charges and generates a detection signal. Furthermore, the CCD image sensor 120 transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals inputted from the CCD image sensor 120, and forms an OCT image of the fundus Ef. An arithmetic process for this is the same as that of a conventional Fourier-Domain-type OCT device.

Further, the arithmetic and control unit 200 controls each part of the retinal camera unit 2, the display device 3 and the OCT unit 100.

As control of the retinal camera unit 2, the arithmetic and control unit 200 executes: control of action of the observation light source 101, the imaging light source 103 and LED's 51 and 61; control of action of the LCD 39; control of movement of the focusing lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; and so on.

The arithmetic and control unit 200 includes a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with a circuit board dedicated for forming OCT images based on detection signals from the CCD image sensor 120. Moreover, the arithmetic and control unit 200 may be provided with operation devices (input devices) such as a keyboard and a mouse, and/or display devices such as LCD.

The retinal camera unit 2, display device 3, OCT unit 100, and arithmetic and control unit 200 may be integrally configured (that is, within a single case), or configured as separate bodies.

[Input Device]

The input device 300 is used in order for the subject to respond during the eyesight measurement. In the eyesight measurement, a predetermined visual target for measuring eyesight is projected onto the eye E. The subject inputs the result of visual confirmation of this target using the input device 300. For example, when a Landolt ring is used as a target, the subject inputs the direction of the rift in the Landolt ring using the input device 300.

Figure 3:
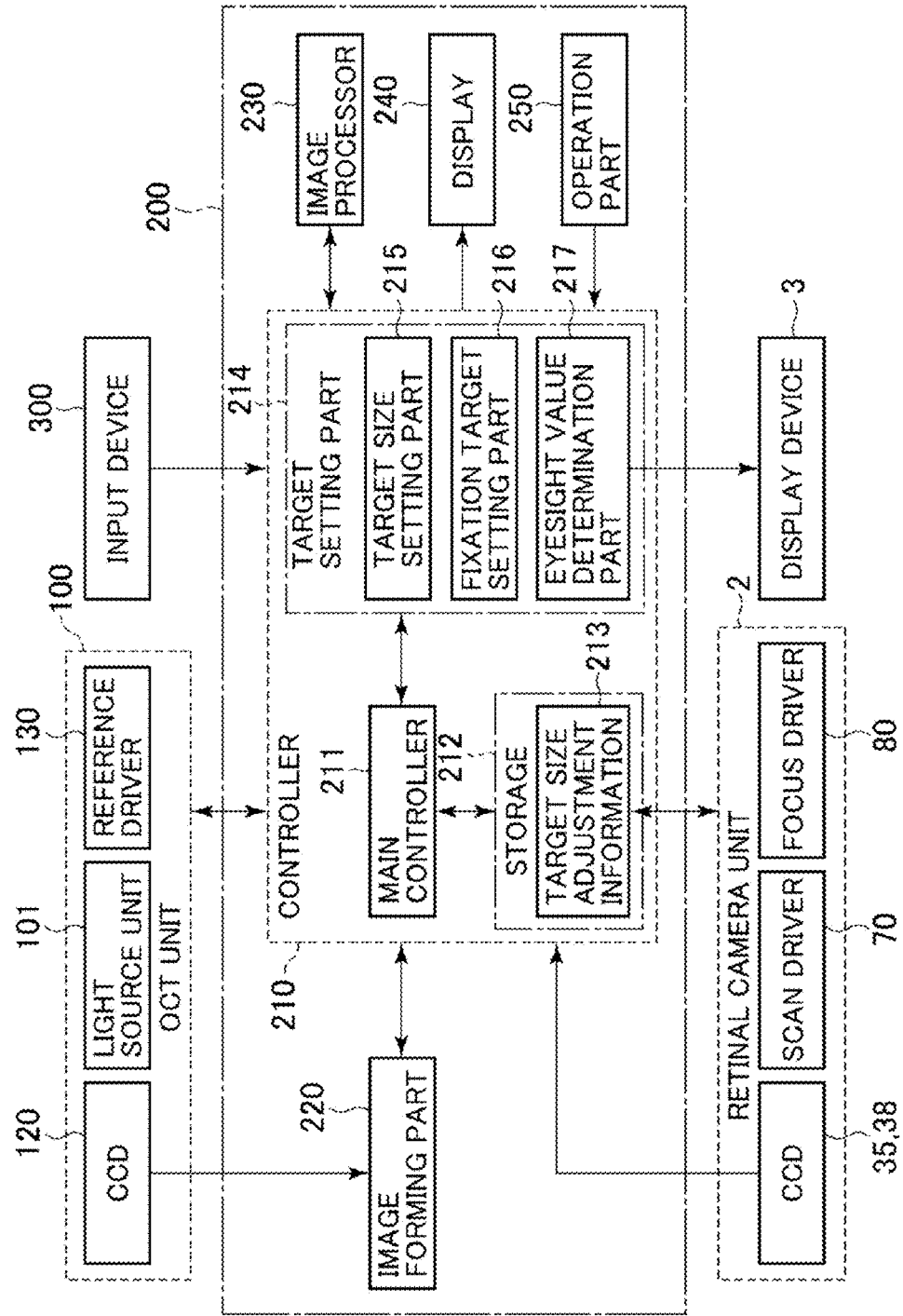
FIG. 3 is a schematic block diagram showing an example of a configuration of an embodiment of a fundus observation apparatus according to the present invention.

The input device 300 is configured, for example, to include a joy stick such as the one shown in FIG. 3. The subject tilts the joystick in the direction corresponding to the result of visual confirmation to the target. The input device 300 transmits an electrical signal corresponding to this operation content (tilting direction) to the arithmetic control unit 200. The input device 300 is one example of the "operation part" of the invention.

[Control System]

A configuration of a control system of the fundus observation apparatus 1 will be described with reference to FIG. 3.

(Controller)

The control system of the fundus observation apparatus 1 has a configuration centered on a controller 210 of the arithmetic and control unit 200. The controller 210 includes, for example, the aforementioned microprocessor, RAM, ROM, hard disk drive, and communication interface. The controller 210 is an example of a "controlling part" of the invention.

A controller 210 is provided with a main controller 211, storage 212 and a target setting part 214. The main controller 211 performs the aforementioned various kinds of control. Specifically, the main controller 211 controls a scan driver 70 as well as a focus driver 80 of the retinal camera unit 2, and further controls a reference driver 130 of the OCT unit 100.

The scan driver 70 is configured, for example, including a servo motor and independently changes the facing direction of the Galvano mirrors 43 and 44. The scan driver 70 consists of one example of the "scanning part" in the invention along with the Galvano mirrors 43 and 44.

The focus driver 80 is configured, for example, including a pulse motor and moves the focusing lens 31 in the optical axis direction. Thereby, the focus position of light towards the fundus Ef is changed.

The reference driver 130 is configured, for example, including a pulse motor and integrally moves the collimator lens 113 as well as the reference mirror 114 along the travelling direction of the reference light LR.

The main controller 211 executes a process of writing data into the storage 212, and a process of reading out the data from the storage 212.

The storage 212 stores various kinds of data. The data stored in the storage 212 is, for example, image data of OCT images, image data of fundus images, and eye information. The eye information includes information on the eye, for example, information on a subject such as a patient ID and a name, information on identification of left eye or right eye, and so on.

Moreover, the eyesight value of the eye E measured by the fundus observation apparatus 1 is stored in the storage 212. Although the details will be described later, this eyesight value is stored in correlation with the OCT image. The storage 212 is one example of the "storage part" of the invention.

It should be noted that the storage part is not limited to storage devices such as hard disk drives and RAM, and may be any recording media writable by a drive device. As this recording media, for example, optical disks, magnetic optical disks (such as CD-R/DVD-RAM/MO), magnetic recording media (such as Floppy Disks®/ZIP), SSDs (Solid State Drives), etc. may also be used.

Moreover, OCT images and eyesight values may be transmitted to the predetermined storage part to be stored via a network such as the Internet and LAN. Furthermore, it is not necessary to store OCT images and eyesight values in the same storage device, and they may be stored in separate storage devices. It should be noted that also in this case, the OCT images and the eyesight values must be correlated with each other.

Furthermore, target size adjustment information 213 is preliminarily stored in the storage 212. The target size adjustment information 213 includes the information that associates the position of the focusing lens 31 with the target size. Hereinafter, the target size adjustment information 213 is described in detail.

In this embodiment, eyesight measurement is conducted on the eye E by projecting the visual target for measuring eyesight displayed on the LCD 39 to the fundus Ef. The eyesight examination is for determining the eyesight values based on the target size that can be visually confirmed. (As a specific example, the eyesight values are determined by presenting various sizes of Landolt rings to the eye E, obtaining a response regarding the direction of the rift in the presented Landolt ring, and then determining whether the response is true or false.)

However, in the configuration in which the target displayed on the LCD 39 is projected on the fundus Ef, even if the size of the target displayed on the LCD 39 is the same, the size of the image projected on the fundus Ef may be different due to the eye refractive power of the eye E. Consequently, the accuracy of the eyesight examination is lowered.

The target adjustment information 213 is referenced in order to avoid a decrease in measurement accuracy due to such a difference in eye refractive power. In this embodiment, as described above, focusing of the optical system on the fundus Ef is accomplished by projecting a split target on the fundus Ef using the focus optical system 60 and moving the focusing lens 31 and the focus optical system 60 based on the position of the split target. The position of the split target is affected by the eye refractive power of the eye E, i.e., the refractive power of the cornea and the lens.

The target size adjustment information 213 includes, as information for making the projection size of the visual target for measuring eyesight onto the fundus independent of the eye refractive power, information that correlates the position of the focusing lens 31 and the size of the visual target for measuring eyesight. For example, information correlating, for the target at each eyesight value, the position of the focusing lens 31 and the display size of the target on the LCD 39 is recorded in the target size adjustment information 213. This information is in the form of a table, graph, mathematical expression, etc.

This information may be created by, for example, a numerical simulation such as a ray trace. Moreover, this information may also be created by actually performing a measurement using an eye model, an eye on a living body or an isolated eye.

It should be noted that the information recorded in the target size adjustment information 213 is not limited to the above. For example, each position of the focusing lens 31 may be correlated with the display size of the target for each eyesight value.

Moreover, the information recorded in the target size adjustment information 213 may be information that correlates the position of the focus optical system 60 and the target size. Here, the focus optical system 60 and the focusing lens 31 are moved in conjunction with each other, with the position of the focus optical system 60 having a one-on-one correspondence with the position of the focusing lens 31. Therefore, this modification example can be considered equivalent to the case in which the position of the focusing lens 31 and the target size are correlated.

Moreover, the information recorded in the target size adjustment information 213 may be the information that correlates the eye refractive power value and the target size. In this case, the eye refractive power value of the eye E that is previously acquired is input, and the target size is adjusted based on the input value. Here, since the eye refractive power value corresponds one-on-one with the position of the focusing lens 31 (at least theoretically), this modification example can also be considered equivalent to the case in which the position of the focusing lens 31 and the target size are correlated.

The target setting part 214 executes various setting processes regarding the target projected on the eye E, such as a visual target for measuring eyesight and a fixation target. The target setting part 214 is provided with a target size setting part 215, a fixation target setting part 216 and an eyesight value determination part 217.

The target size setting part 215 acquires the position information of the focusing lens 31 and obtains the size of the visual target for measuring eyesight based on the position information and the target size adjustment information 213.

An example of a process for acquiring the position information of the focusing lens 31 is described. The focusing lens 31 is, as described above, moved by the focus drive 80 based on the control by the main controller 211. Consequently, based on the control content (control history) by the main controller 211, the position information of the focusing lens 31 can be acquired. More specifically, when the focus drive 80 includes a pulse motor, the position information of the focusing lens 31 can be acquired with reference to the pulse number transmitted from the main controller 211 to the focus drive 80. Moreover, it is also possible to use a detector (for example, a potentiometer) that detects the position of the focusing lens 31.

Upon acquisition of the position information of the focusing lens 31, the target size setting part 215 obtains the target size corresponding to that position information with reference to the target size adjustment information 213.

The fixation target setting part 216 performs setting regarding the fixation target displayed on the LCD 39. Specifically, the fixation target setting part 216 sets the display position of the fixation target on the LCD 39. For example, the fixation target setting part 216 sets the display position of the fixation target on the LCD 39 based on the region for scanning with signal light LS (scanning region; described later) using Galvano mirrors 43, 44. The operational example of the fixation target setting part 216 will be described later.

The eyesight value determination part 217 executes various processes for obtaining the eyesight value of the eye E. As these processes, for example, conventional approaches are applicable in which the visual targets for measuring eyesight corresponding to various eyesight values are automatically switched to be presented to the eye. (For example, see republished No. 03/041571.) Hereinafter, an operational example of the eyesight value determination part 217 is described.

First, the eyesight value determination part 217 determines the visual target for measuring eyesight to be first presented to the eye E. As a target to be first presented, a target corresponding to the predetermined eyesight value is selected. This first target is a target corresponding to, for example, the eyesight value 0.1.

Moreover, when previously measured eyesight values can be acquired for this eye E, the first target can be determined based on this information. For example, when the previously obtained eyesight value for the above eye E is 0.7, a target corresponding to an eyesight value lower than that value (for example, 0.5) by a predetermined value is selected as the first target.

Previous eyesight values may be input using, for example, the operation part 250, or may be obtained from, for example, an electronic medical record system through, for example, LAN. Moreover, previous eyesight values can be correlated to the above-mentioned information on the eye and stored in the storage 212. In addition, the previous eyesight value referenced in this examination is preferably the newest among the previously measured eyesight values. When the previous eyesight value is obtained from the electric medical record system, it is possible to selectively obtain the newest eyesight value with reference to the medical examination date recorded in the electric medical records.

Furthermore, the eyesight value determination part 217 determines the target to be presented next, based on the response to the target presented to the eye E from the subject. For this process, for example, the same process as the conventional process can be used. For example, if a correct answer is obtained twice for targets with a certain eyesight value, then a target with the next higher eyesight value is selected. In contrast, if a wrong answer is obtained twice for targets with a certain eyesight value, then a target with the next lower eyesight value is selected.

Furthermore, the eyesight value determination part 217 determines the eyesight value of the eye E based on the response content from the subject according to the change in the target size. This process is, for example, executed similarly to the conventional process. For example, if a correct answer is obtained twice for targets with a certain eyesight value, and a wrong answer is obtained twice for targets with a next higher eyesight value, then the former certain eyesight value is determined as the eyesight value for the eye E. Moreover, if a correct answer is obtained twice for targets at the highest presentable eyesight value (for example, 2.0), that highest eyesight value is determined as the eyesight value for the eye E. Furthermore, if a wrong answer is obtained twice for targets with the lowest presentable eyesight value (for example, 0.1), the result is that the eyesight value is unmeasurable or less than a predetermined value.

The target setting part 214 may be configured such that it can set the display position of the visual target for measuring eyesight on the LCD 39.

(Image Forming Part)

An image forming part 220 forms image data of a tomographic image of the fundus Ef based on the detection signals from the CCD image sensor 120. Like the conventional Fourier-Domain OCT, this process includes processes such as noise elimination (noise reduction), filtering, and FFT (Fast Fourier Transform).

The image forming part 220 includes, for example, the aforementioned circuit board and communication interface. It should be noted that "image data" and the "image" presented based on the image data may be identified with each other in this specification.

(Image Processor)

An image processor 230 executes various image processing and analysis on images formed by the image forming part 220. For example, the image processor 230 executes various correction processes such as luminance correction and dispersion correction of images.

Further, the image processor 230 executes, for example, an interpolation process of interpolating pixels between tomographic images formed by the image forming part 220, thereby forming image data of a three-dimensional image of the fundus Ef.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a three-dimensional coordinate system (namely, embedding into a three-dimensional space).

The image processor 230 includes, for example, the aforementioned microprocessor, RAM, ROM, hard disk drive, circuit board, and so on.

The image forming part 220 (and the image processor 230) is an example of the "image forming part" of the invention.

(Display and Operation Part)

The display 240 is configured including a display device of the aforementioned arithmetic and control unit 200. The operation part 250 is configured including an operation device of the aforementioned arithmetic and control unit 200. Furthermore, the operation part 250 may also include various kinds of buttons or keys provided with the case of the fundus observation apparatus 1 or its outside. For example, if the retinal camera unit 2 has a case that is the same as conventional fundus cameras, a joy stick, operation panel, etc. provided with the case may also be included in the operation part 250. Furthermore, the display 240 may also include various display devices such as a touch panel monitor, etc. provided with the case of the retinal camera unit 2.

The display 240 and the operation part 250 do not need to be composed as separate devices. For example, like a touch panel LCD, a device in which the display function and the operation function are integrated can be used.

[Scan with Signal Light and OCT Image]

A scan with the signal light LS and an OCT image will be described.

The scan aspect of the signal light LS by the fundus observation apparatus 1 is, for example, a horizontal scan, vertical scan, cruciform scan, radial scan, circular scan, concentric scan, and helical scan. These scan aspects are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory while making the turning radius gradually smaller (or greater).

With the configuration as described before, the Galvano mirrors 43 and 44 are capable of scanning with the signal light LS in the x-direction and the y-direction independently, and is therefore capable of scanning with the signal light LS along an arbitrary trajectory on the xy-plane. Thus, it is possible to realize various types of scan aspects as described above.

By scanning the signal light LS in the mode described above, it is possible to form tomographic images of the depthwise direction (z-direction) along scanning lines (scan trajectory). Moreover, in a case that the interval between scanning lines is narrow, it is possible to form the aforementioned three-dimensional image.

A region on the fundus Ef subjected to scanning by the signal light LS as above is referred to as a scanning region. For example, a scanning region in three-dimensional scanning is a rectangular-shaped region in which a plurality of horizontal scans are arranged. Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

[Operation]

Figure 4:
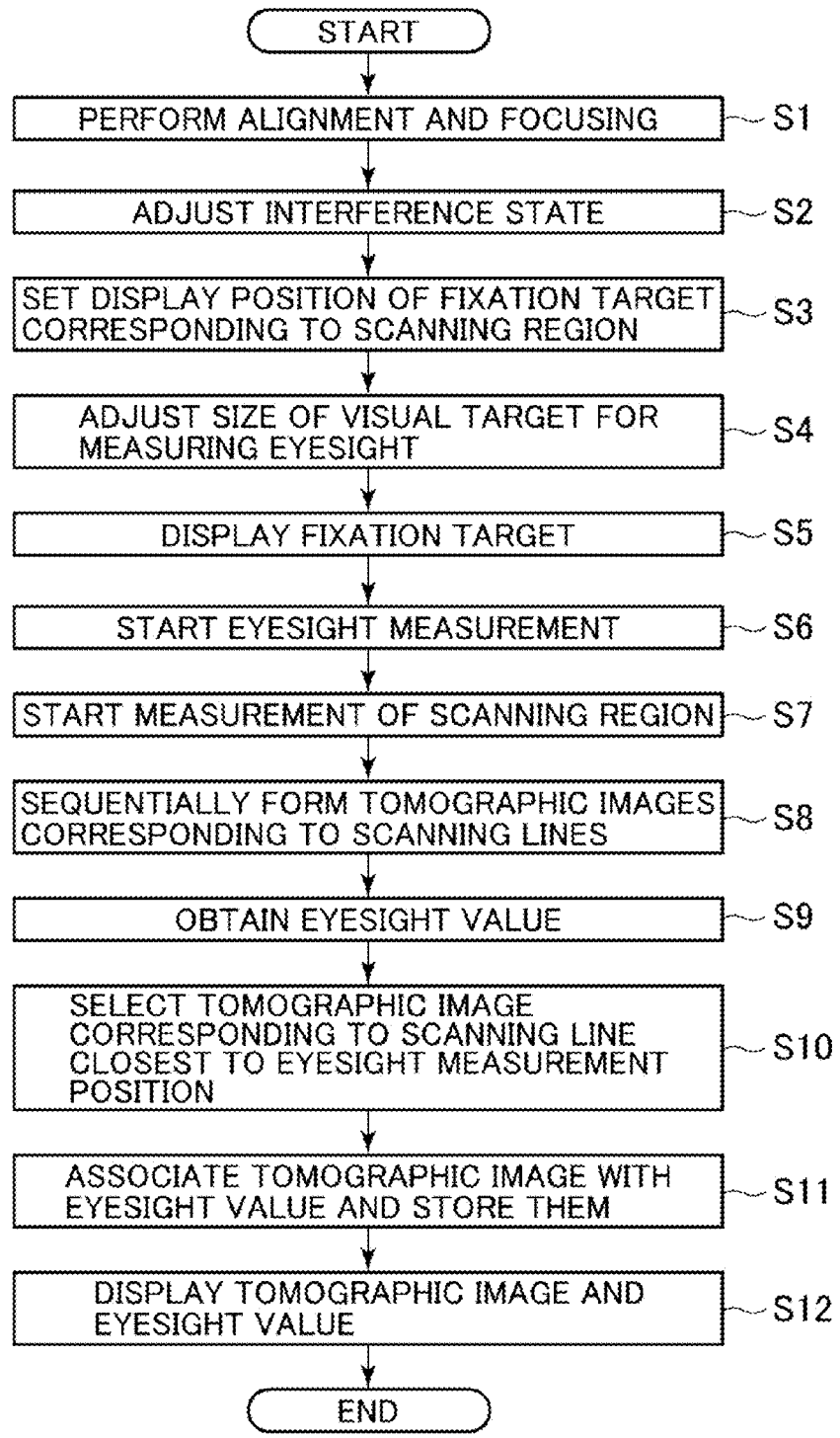
FIG. 4 is a flowchart showing an example of an action of an embodiment of a fundus observation apparatus according to the present invention.

The operation of the fundus observation apparatus 1 is described. The flow chart shown in FIG. 4 represents an example of the operation of the fundus observation apparatus 1.

First, as in the conventional manner, the main controller 211 controls, for example, the alignment optical system 50 to perform alignment to the eye E, and also controls, for example, the focus optical system 60, the focus drive 80, etc., to perform focusing on the fundus Ef (S1).

Next, the main controller 211 adjusts the position of the reference mirror 114 (as well as the position of the collimator lens 113) to adjust the interference state of the signal light LS and the reference light LR (S2). At this time, adjustment is made so that the image of the desired depthwise position of the fundus Ef becomes clear. Moreover, it is desirable to adjust the position of the reference mirror 114 so that the image of the predetermined depthwise position (for example, the retina surface) is located within a predetermined range in the frame. It should be noted that the position adjustment of the reference mirror 114 may be manually performed using the operation part 250 or may be automatically performed.

Upon completion of the adjustment of the interference state, the fixation target setting part 216 sets the display position of the fixation target on the LCD 39 corresponding to the predetermined scanning region (for example, a rectangular region for three-dimensional scanning) (S3). It should be noted that the scanning region is set, for example, before or after step 1.

Furthermore, the fixation target setting part 215 adjusts the size of the visual target for measuring eyesight based on the position of the focusing lens 31, which is moved during focusing in step 1, and the target size adjustment information 213 (S4).

The main controller 211 controls the LCD 39 to display the fixation target in the display position set in step 3 and fixate the eye E (S5). Furthermore, the main controller 211 allows the first visual target for measuring eyesight, of which the size has been adjusted in step 4, to be displayed on the LCD 39, and begins the eyesight measurement (S6). This eyesight measurement is for measuring the eyesight at the position on the fundus Ef (i.e., projection position of the fixation target) corresponding to this fixation position.

Figure 5:
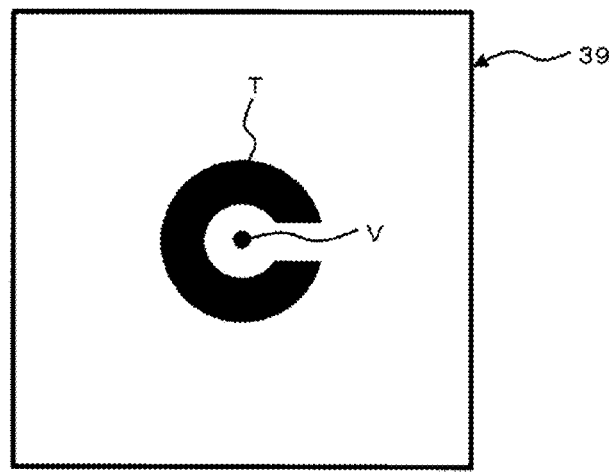
FIG. 5 is a schematic view for explaining an example of an action of an embodiment of a fundus observation apparatus according to the present invention.

In this operational example, as shown in FIG. 5, the fixation target V is displayed in the central position of the display screen of the LCD 39, and the Landolt ring T is displayed such that the central position of the Landolt ring T matches the position of the fixation target V.

At the same time as the start of the eyesight examination, the main controller 211 controls the light source unit 101 and the Galvano mirrors 43 and 44 to begin the measurement in the predetermined scanning region (for example, three-dimensional scanning) (S7).

Figure 6:
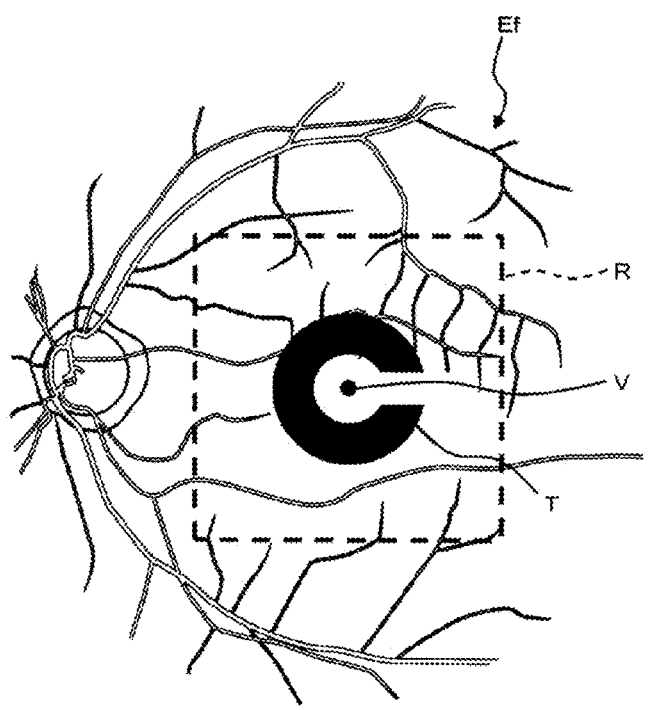
FIG. 6 is a schematic view for explaining an example of an action of an embodiment of a fundus observation apparatus according to the present invention.

The positional relationship between the scanning region of the signal light LS and the target projection region on the fundus Ef is shown in FIG. 6. In this operational example, as in the FIG. 5, the fixation target V is projected on the central position of the projection region of the Landolt ring T, and furthermore, the projection region of the fixation target V is matched to the central position of the scanning region R (rectangular region). It should be noted that the fixation target displayed on the LCD 39 and the projected image of this fixation target on the fundus Ef are denoted by the same symbol V, and the Landolt ring displayed on the LCD 39 and the projected image of this Landolt ring on the fundus Ef are denoted by the same symbol T.

Such a projection mode is achieved, for example, as follows. First, the central position of the display screen of the LCD 39 is placed on an optical axis of the imaging optical system 30. Moreover, the scanning region R is set such that its central position is located on the optical axis of the imaging optical system 30. Therefore, by displaying the fixation target V in the central position of the display screen of the LCD 39 and setting this scanning region R as such, the central position of the scanning region R is matched to the projection region of the fixation target V (i.e., both are placed on the extended line of the optical axis). Furthermore, since the Landolt ring T is displayed on the LCD 39 such that its central position is placed in the central position of the display screen, the central position of the Landolt ring T, the projection region of the fixation target V and the central position of the scanning region R are matched on the fundus Ef.

The controller 210 executes the eyesight measurement at the position of the fundus Ef projected with the fixation target V while scanning the scanning region R with the signal light LS. At this time, the signal light LS is used to sequentially scan a plurality of lines of horizontal scanning (scanning lines) included in the three-dimensional scanning. Then, the image forming part 220 forms a tomographic image corresponding to each scanning line based on the detection results of interference light LC of the signal light LS and the reference light LR (S8). Tomographic images that are formed sequentially are stored in the storage 212 while being correlated with position information of corresponding scanning line (scanning position information). The scanning position information is, for example, information based on the control to the scan drive 70 (i.e., the direction of the Galvano mirrors 43, 44). When the scanning along all scanning lines is completed, the scanning may be ended or similar scanning may be executed again. Here, the eyesight measurement is executed by the eyesight value determination part 217 in the manner described above.

When the eyesight value is obtained by the eyesight value determination part 217 (S9), the main controller 211 selects a tomographic image corresponding to the scanning line closest to the eyesight measurement position (the position projected with the fixation target V) (S10), and stores this tomographic image and the eyesight value in the storage 212 while correlating them with each other (S11). Here, the selection process of the tomographic image is executed with reference to the above-mentioned scanning position information.

The main controller 211 allows the tomographic image and the eyesight value to be displayed on the display device 3 (or the display 240) (S12). Consequently, the examiner can observe the tomographic image of the fundus Ef at the eyesight measurement position.

In this operational example, examination at the fixation position is conducted as described above. Therefore, for the eye E that has no disorder in the macula flava (including a healthy eye), the eyesight value and the tomographic image in the macula flava are generally obtained. On the other hand, for the eye E that has, for example, a disorder in the macula flava, the fixation target V tends to be viewed by the site having the highest visual ability in the fundus Ef (other than the macula flava), so the eyesight value and the tomographic image in such a site are generally obtained.

Instead of conducting an examination on the fixation position in this way, it is also possible to conduct an examination on the site of interest (treatment site, diagnosed site, etc.) other than the fixation position. To this end, as described in detail in the following operational example, it is effective to conduct an examination under the condition that the display position of the fixation target V is shifted from the display position of the visual target for measuring eyesight on the LCD 39.

[Another Operational Example]

Figure 7:
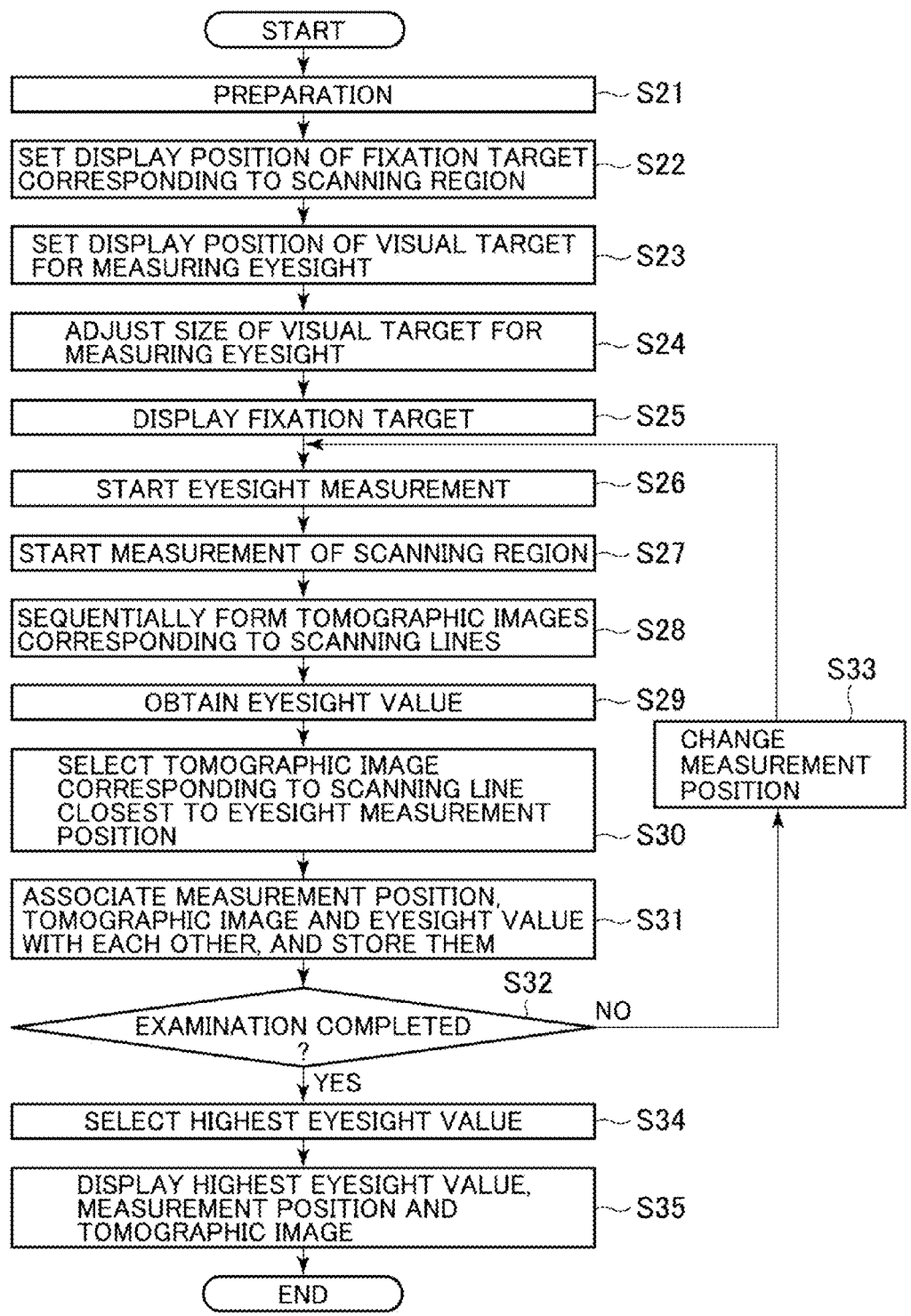
FIG. 7 is a flowchart showing an example of an action of an embodiment of a fundus observation apparatus according to the present invention.

In this operational example, eyesight measurement is conducted on various positions in the fundus Ef by changing the relative position of the projection region of the visual target for measuring eyesight and the projection region of the fixation target, and furthermore, a tomographic image covering the eyesight measurement position is obtained. Hereinafter, the operational example shown in the flowchart shown in FIG. 7 is described.

As a preliminary stage of the examination, as in the operational example described above, the alignment, focusing, determination of the scanning region, and adjustment of the interference state are performed (S21).

The fixation target setting part 216 sets the display position of the fixation target on the LCD 39 corresponding to the scanning region (for example, a rectangular region for three-dimensional scanning) (S22). Moreover, the target setting part 214 sets the display position of the visual target for measuring eyesight on the LCD 39 (S23). Furthermore, the target size setting part 215 adjusts the size of the visual target for measuring eyesight based on the position of the focusing lens 31 after focusing and the target size adjustment information 213 (S24).

Figure 8:
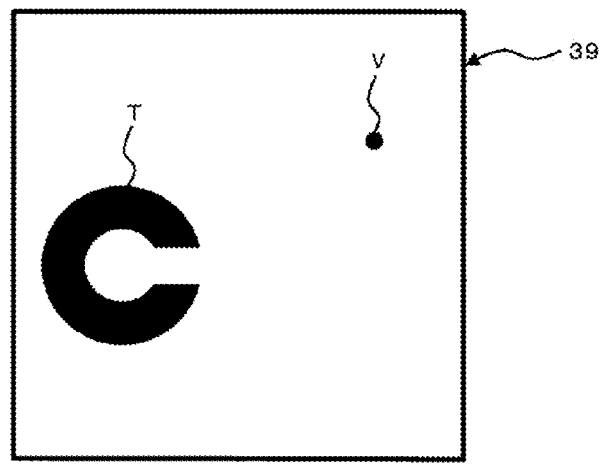
FIG. 8 is a schematic view for explaining an example of an action of an embodiment of a fundus observation apparatus according to the present invention.

It should be noted that, in this operational example, as opposed to the case shown in FIG. 5, it is not necessary to display the fixation target on the central position of the display screen, and furthermore, it is not necessary to match the central position of the visual target for measuring eyesight to the position of the fixation target. For example, as shown in FIG. 8, the fixation target V is displayed in a position deviating from the central position of the display screen of the LCD 39, and the Landolt ring T is displayed with its central position deviating from the position of the fixation target V. It should be noted that, in the example shown in FIG. 8, the display positions of the fixation target V and the Landolt ring T both deviate from the central position of the display screen, but one of these positions may be displayed in this central position while the other is displayed in other positions.

The important point here is that the fixation target V and the Landolt ring T are displayed in different positions. Specifically, when the fixation target V and the Landolt ring T are displayed in different positions, on the assumption that the eye E is fixed by the fixation target V, the eyesight in the position on the fundus Ef that is different from the fixation position can be measured. (In the above operational example, the eyesight in the fixation position is measured.) Moreover, by changing the relative position of the fixation target V and the Landolt ring T, eyesight in various positions on the fundus Ef can be measured.

The main controller 211 controls the LCD 39 to display the fixation target in the display position set in step 22 and fix the eye E (S25). Furthermore, the main controller 211 controls the LCD 39 to display the first visual target for measuring eyesight in the display position set in step 23, and begins the eyesight measurement (S26).

At the same time as the start of the eyesight measurement, the main controller 211 begins the measurement in the scanning region (for example, three-dimensional scanning) (S27).

Figure 9:
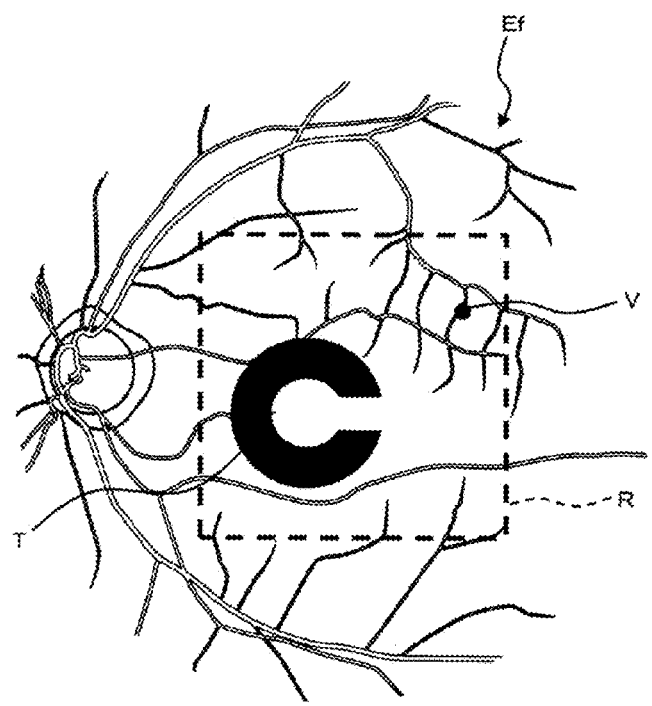
FIG. 9 is a schematic view for explaining an example of an action of an embodiment of a fundus observation apparatus according to the present invention.

The positional relationship between the scanning region of the signal light LS and the target projection region on the fundus Ef is shown in FIG. 9. In this operational example, as in FIG. 8, the fixation target V and the Landolt ring T are projected at different positions. Moreover, as in the operational example described above (FIG. 6), the scanning region R is set such that its central position is located on the optical axis of the imaging optical system 30. Consequently, the fixation target V and the Landolt ring T are projected at a position different from the central position of the scanning region R. It should be noted that, as described above, when the fixation target V or the Landolt ring T is displayed at the central position of the display screen of the LCD 39, the target displayed at this central position is projected at the central position of the scanning region R.

The controller 210 executes the eyesight measurement on the position of the fundus Ef projected with the Landolt ring T while scanning the scanning region R with the signal light LS. At this time, the signal light LS is used to sequentially scan a plurality of scanning lines included in the three-dimensional scanning. The image forming part 220 forms a tomographic image corresponding to each scanning line (S28). Tomographic images that are formed sequentially are stored in the storage 212 while being correlated with the scanning position information. The scanning position information is, for example, information based on the control to the scan drive 70 (i.e., the direction of the Galvano mirrors 43, 44). When the scanning along all scanning lines is completed, the scanning may be ended or similar scanning may be executed again. Here, the eyesight measurement is executed by the eyesight value determination part 217 in the manner described above.

When the eyesight value of this measurement position is obtained (S29), the main controller 211 selects a tomographic image corresponding to the scanning line closest to the eyesight measurement position (S30), and stores the measurement position, the tomographic image and the eyesight value in the storage 212 while correlating them with each other (S31). Here, the correlation of the tomographic image and the eyesight value can be achieved similarly to the above operational example. Moreover, the measurement position can be determined based on, for example, the relative position of the fixation target V and the Landolt ring T (the relative position of both display positions).

If the examination is not completed at all the measurement positions (S32: No), the target setting part 214 sets the display positions of the fixation target V and the Landolt ring T on the LCD 39 corresponding to the next measurement position. The main controller 211 allows the fixation target V and the Landolt ring T to be displayed at the set display positions. Consequently, each projection region of the fixation target V and the Landolt ring T on the fundus Ef is changed. Under the condition that the eye E is fixed by this fixation target V, the Landolt ring T is projected at the next measurement position described above (S33). Then, the eyesight measurement at this new measurement position is started (S26). At this time, scanning with the signal light LS may be executed again (S27).

It should be noted that, when the new measurement position deviates from the prior scanning region R, the controller 210 newly sets the scanning region to include the new measurement position (i.e., so that a new projection region of the Landolt ring T is overlapped), and performs scanning with the signal light LS to form a tomographic image.

The change in the measurement position as described above is, for example, sequentially executed for a predetermined number of positions. As a specific example, the eyesight measurement is first conducted on the central position of the scanning region R as shown in FIG. 6, and then the eyesight measurement is further conducted on each apex position of a rectangle enclosing this central position.

Moreover, it is also possible to set the measurement position based on the condition of the eye E. For example, it is also possible to set the site of interest and its peripheral position of the eye E as the measurement position. Such a measurement position can be set based on, for example, the positional relationship of the site of interest relative to the macular area. Moreover, this positional relationship can be obtained based on, for example, the fundus image. In addition, it is also possible to set the measurement position so as to avoid the region on the fundus Ef that is thought to have low eyesight (for example, a region affected due to cataracts, a region that has an untreatable retinal disease, etc.)

When the examination of all measurement positions is completed (S32: Yes), the main controller 211 selects the highest value among the acquired eyesight values (S34). The main controller 211 allows the selected eyesight value and the measurement position and tomographic image correlated to this eyesight value to be displayed on the display device 3 (or the display 240) (S35). Consequently, the examiner can recognize the site having good eyesight on the fundus Ef, and furthermore, can observe the tomographic image of the fundus Ef at this site.

When such an examination is applied at follow-ups, the measurement position in which the highest eyesight value is obtained may be changed. For example, in the follow-ups after the treatment of the disease in the macula flava, the highest eyesight value is obtained first at a site other than the macula flava, and then, in the course of treatment, the highest eyesight value may be obtained in the macula flava. In this way, therapeutic effect may appear not only as the improvement of the eyesight value, but also the change in the measurement position in which the highest eyesight value is obtained. Moreover, it is also possible to specify the measurement position at which the highest eyesight value is obtained as an actual fixation position.

[Actions and Effects]

The actions and effects of the fundus observation apparatus 1 as described above will be described.

According to the fundus observation apparatus 1, it is possible to execute the OCT measurement and the eyesight measurement while superposing the scanning region R of the signal light LS on the projection region of the visual target for measuring eyesight (Landolt ring T) to form the tomographic image of the fundus Ef at the scanning region R, and it is also possible to store the eyesight value measured using the Landolt ring T and the tomographic image while correlating them to each other.

Here, the fundus observation apparatus 1 controls the LCD 39 based on the scanning region R of the signal light LS to superpose the projection region of the Landolt ring T on the fundus Ef on the scanning region R. Furthermore, the fundus observation apparatus 1 can display the fixation target V on the LCD 39 along with the Landolt ring T to project them on the fundus Ef, and changes the projection region of the Landolt ring T on the fundus Ef by changing the relative display position of the Landolt ring T and the fixation target V based on the scanning region R.

According to such the fundus observation apparatus 1, it is possible to acquire an image (tomographic image) of the eyesight measurement site in the fundus Ef. In particular, when the projection region and the scanning region are set to include a site of interest in the fundus Ef, the tomographic image and the eyesight value of that site of interest can be acquired. Consequently, the condition of the eyesight and the morphology of the retina, etc., can be recognized, and furthermore, their relationship can also be recognized.

For example, even if the morphology of the retina is improved, the patient cannot realize the therapeutic effect unless the eyesight is improved. By using the fundus observation apparatus 1, it is possible to closely investigate whether or not such a situation has occurred.

Moreover, the fundus observation apparatus 1 allows different sizes of visual targets for measuring eyesight to be displayed on the LCD 39 to change the size of the projection region on the fundus Ef, thereby making it possible to project the visual target for measuring eyesight corresponding to different eyesight values on the fundus Ef. It should be noted that the size of the projection region on the fundus Ef can also be changed with a target of the same size being displayed by providing an optical element such as a lens between the LCD 39 and the eye E.

Furthermore, the fundus observation apparatus 1 can adjust the size of the visual target for measuring eyesight displayed on the LCD 39 based on the position of the focusing lens 31. It should be noted that, in place of adjusting the display size, the size of the projection region may be changed by the optical element described above.

With such a configuration, it is possible to precisely measure the eyesight value without being affected by the eye refractive power of the eye E.

Moreover, the fundus observation apparatus 1 is configured to change the size of the visual target for measuring eyesight displayed on the LCD 39 based on the response contents from the subject against the visual target for measuring eyesight presented to the eye E, and furthermore, to determine the eyesight value of the eye E based on the response contents according to the change of the visual target for measuring eyesight.

With such a configuration, it is possible to automatically measure the eyesight at a predetermined site in the eye E (macula flava, site of interest, etc.).

Moreover, the low-coherence light L0 used in the OCT measurement by the fundus observation apparatus 1 is preferably invisible light. By using such invisible light, even when the eyesight measurement and the OCT measurement are conducted simultaneously, the signal light LS is not visually recognized by the subject. Consequently, the complexity in the examination can be reduced and the examination can be smoothly conducted, thereby further improving the accuracy and precision of the examination results. It should be noted that it is necessary for the subject to visually confirm the fixation target and the visual target for measuring eyesight.

Furthermore, the invisible light used in the OCT measurement is preferably near-infrared light of center wavelength within the range from about 1050 to 1060 nm. Here, if the center wavelength is shorter than 1050 nm, there is a risk that the signal light LS may not certainly reach the fundus Ef. On the other hand, if the center wavelength is longer than 1060 nm, there is a risk that the signal light LS will be absorbed by the water content within the eyeball so that it may not certainly reach the fundus Ef.

The configuration described above is merely one example for favorably implementing the present invention. Therefore, it is possible to properly make arbitrary modification within the scope of the present invention.

In the above embodiment, the configuration in which the projection region of the visual target for measuring eyesight on the fundus is superposed on the scanning region by controlling the display part based on the scanning region of the signal light, but it is also possible to apply a configuration for performing the opposite process. Specifically, it is possible to apply a configuration in which the scanning region of the signal light on the fundus is superposed on the projection region of the visual target for measuring eyesight by controlling the scanning part based on the display position of the visual target for measuring eyesight on the display part.

Figure 10:
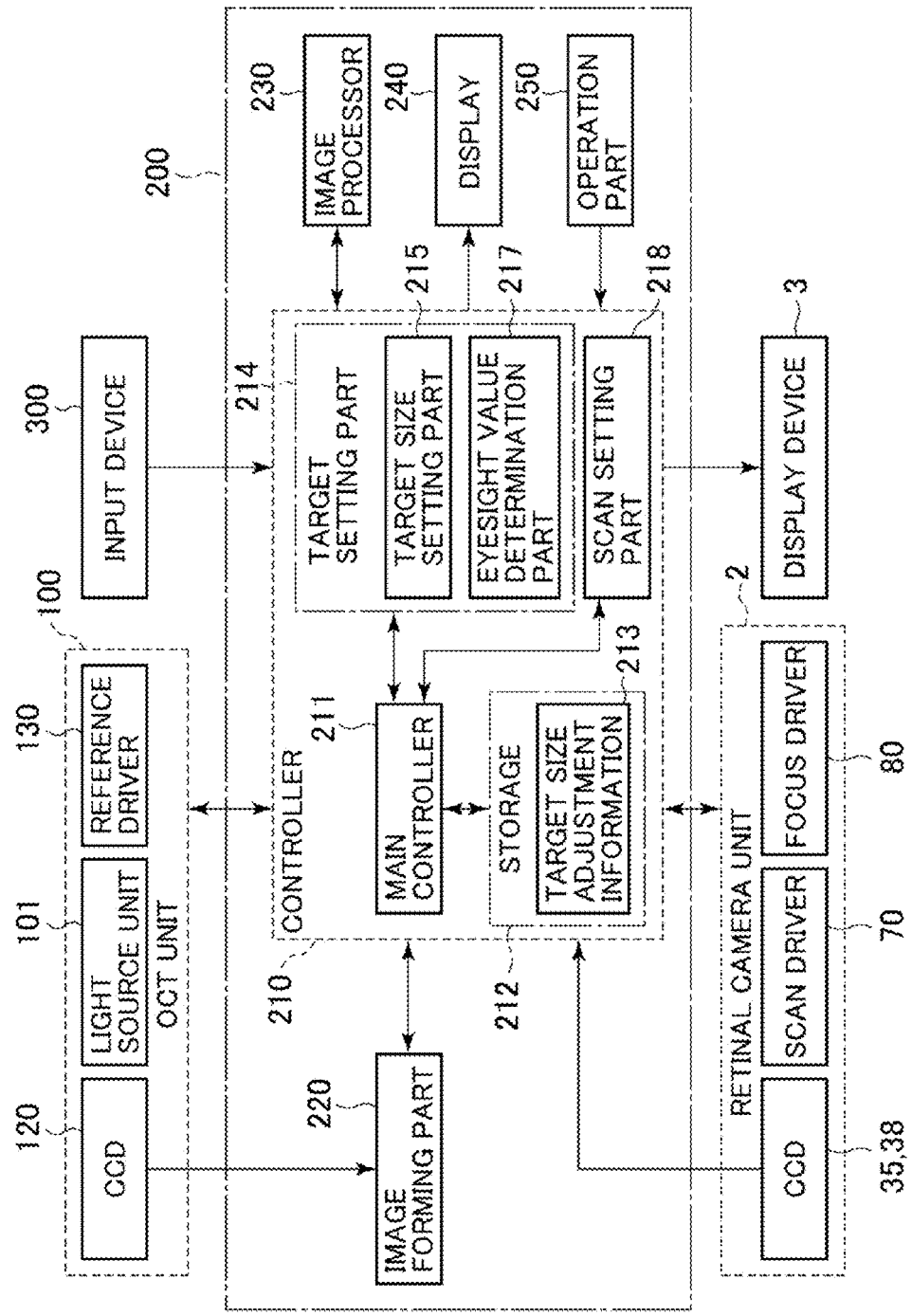
FIG. 10 is a schematic block diagram showing an example of a configuration of a modification example of an embodiment of a fundus observation apparatus according to the present invention.

Such a configuration is shown in FIG. 10. It should be noted that the retinal camera unit 2 and the OCT unit 100 have the same configuration as that in the above embodiment (refer to FIG. 1, FIG. 2).

Moreover, it is possible to apply various configurations described in the above embodiments to this modification example. For example, it is possible to apply the configuration in which the visual targets for measuring eyesight corresponding to various eyesight values is presented, the configuration in which the size of the visual target for measuring eyesight is adjusted, the configuration in which the eyesight value is automatically obtained, the configuration for the light source, etc.

The block diagram shown in FIG. 10 is almost the same as that shown in FIG. 3. However, it is different from the configuration in FIG. 3 in that the controller 210 of this modification example is provided with a scan setting part 218 and in that the fixation target setting part 216 is not provided. It should be noted that the fixation target setting part 216 may also be provided in this modification example.

The scan setting part 218 performs setting in regard to scanning with the signal light LS. Specifically, the scan setting part 218 sets the scanning region of the signal light LS by the Galvano mirrors 43, 44. For example, the scan setting part 218 sets the scanning region based on the display position of the visual target for measuring eyesight on the LCD 39 so that the projection region of the visual target for measuring eyesight and the scanning region are overlapped with each other.

An operation example of the scan setting part 218 is described. The display position of the visual target for measuring eyesight on the LCD 39 can be recognized by the main controller 211 because it is controlled by the main controller 211. For example, when the central position of the display screen of the LCD 39 is located on an optical axis of the imaging optical system 30, the display position of the target can be recognized as a displacement of the central position of the target relative to the central position of the display screen. Moreover, the display region of the target on the display screen can be recognized based on the display size of the target.

Furthermore, the direction of each of the Galvano mirrors 43, 44 can be recognized by the main controller 211. Specifically, the main controller 211 can recognize the position (reference position) of each Galvano mirror 43, 44 for directing the signal light LS such that it is guided in a direction parallel with the optical axis.

Moreover, the scanning mode of the signal light LS (three-dimensional scanning, radial scanning, etc.) is selected beforehand, and the scan setting part 218 sets the position of the scanning region in the selected scanning mode based on the display position of the target.

When achieving the condition shown in FIG. 6, since the Landolt ring T and the fixation target V are displayed on the optical axis, the scan setting part 218 sets a rectangular scanning region R centered on the reference position of the Galvano mirrors 43, 44. The main controller 211 allows the Landolt ring T and the fixation target V to be displayed at the central position of the LCD 39, and also controls the scan drive 70 to sequentially scan with the signal light LS along a plurality of scanning lines included in the set scanning region R. Consequently, as shown in FIG. 6, it is possible to conduct the examination with the scanning region R and the Landolt ring T overlapped with each other.

Moreover, when achieving the condition shown in FIG. 9, since the Landolt ring T and the fixation target V are displayed at any position on the display screen, the scan setting part 218 sets the scanning region R (i.e., the driving range of the Galvano mirrors 43, 44) so that it is superposed on the projection region of the Landolt ring T based on the display position of the Landolt ring T. The main controller 211 allows the Landolt ring T and the fixation target V to be displayed on the LCD 39, and also controls the scan drive 70 to sequentially scan with the signal light LS along a plurality of scanning lines included in the set scanning region R. Consequently, as shown in FIG. 9, it is possible to conduct the examination with the scanning region R and the Landolt ring T overlapped with each other.

According to such a modification example, it is possible to acquire an image of the eyesight measurement site in the fundus Ef. It should be noted that in the above embodiment the examination is conducted by setting the projection region of the target superposed on the preliminarily set scanning region, but in this modification example, conversely, the examination can be conducted by setting the scanning region superposed on the preliminarily set projection region of the target.

In the above embodiment, the Landolt ring is used as the visual target for measuring eyesight, but it is possible to apply various targets other than this. For example, the target pattern can be changed such as by displaying various characters. Moreover, the target is not limited to a still image, and may be a moving image. Moreover, it may be configured so that not only the size of the target but also various presentation modes can be changed. For example, it is possible to change the color or brightness (contrast) of the target.

In the above embodiment, the tomographic image and the eyesight value are stored while being correlated to each other, but the OCT image correlated to the eyesight value is not limited to a tomographic image. For example, a three-dimensional image obtained by three-dimensional scanning and an eyesight value can also be stored while being correlated to each other. In this case, it is possible to recognize the three-dimensional positional relationship between the site of interest in the fundus Ef and the fixation position. Moreover, it is also possible to recognize the size (area or volume) of the affected site. By making it possible to acquire such information, the therapeutic effect can be assessed in more detail than in the case in which two-dimensional tomographic images are captured.

Moreover, it is also possible to form a tomographic image on any cross-section passing near the eyesight measurement position based on the volume data obtained by the three-dimensional scanning and store this tomographic image and the eyesight value while correlating them with each other. This tomographic image is formed by the image processor 230.

In the above embodiment, the OCT measurement is started at the same time as the start of the eyesight measurement, but the start timing of these two operations may be of any timing. For example, since the eyesight measurement takes more time than the OCT measurement, the OCT measurement may start in the course of the eyesight measurement. Moreover, it is sufficient if the OCT measurement is executed at least once for one scanning region.

When the configuration of above embodiment is utilized, the following OCT measurement can be performed. In this OCT measurement, the actual fixation position of the eye E is identified by performing scanning with the signal light LS in two steps.

In the first step, a scanning mode that can be executed for a relatively short time is applied, while in the second step, a scanning mode that can form a three-dimensional image is applied. It should be noted that it is possible to reverse the first step and the second step.

As a specific example, the case in which cruciform scanning is applied in the first step and three-dimensional scanning is applied in the second step is described. In the first step, a fixation target is first presented to an eye E for fixation. Then, OCT measurement by cruciform scanning is performed on the fundus Ef of the fixed eye E to form a tomographic image corresponding to horizontal scanning (horizontal tomographic image) and a tomographic image corresponding to vertical scanning (vertical tomographic image). Here, since cruciform scanning is executed instantly, it is believed that there is no deviation of the fixation position of the eye E during the measurement.

Next, as the second step, OCT measurement by three-dimensional scanning is performed on the eye E fixed by the same fixation target as that in the first step to form a plurality of tomographic images corresponding to a plurality of horizontal scanning (scanning lines). Moreover, the image processor 230 generates volume data or stack data based on these tomographic images. Since three-dimensional scanning takes some time (on the order of a few seconds), the fixation position of the eye E may deviate during the measurement.

Subsequently, the image processor 230 calculates the image correlation between the horizontal tomographic image acquired in the first step and each tomographic image acquired in the second step, and identifies the cross-sectional position of the tomographic image in the second step with the highest correlation value. At this time, the correlation value between various cross-sectional images in the horizontal direction of the volume data generated in the second step and the horizontal tomographic image may be calculated and the cross-sectional position in the horizontal direction of the volume data with the highest correlation value may be identified.

Similarly, the image processor 230 calculates the image correlation between the vertical tomographic image acquired in the first step and various cross-sectional images in the vertical direction of the volume data acquired in the second step, and identifies the cross-sectional position in the vertical direction of the volume data with the highest correlation value.

The crossing position of the horizontal cross-sectional position and the vertical cross-sectional position in the three-dimensional image as identified above is the fixation position of the eye E. Consequently, the fixation position of the eye E on the three-dimensional image acquired in the second step can be easily identified. Furthermore, three-dimensional morphology of the fundus Ef near this fixation position can be recognized, allowing the recognized information to possibly aid in diagnosis and treatment.

A modification example in which the OCT measurement is performed based on the eyesight measurement results is described. In this modification example, a visual target for measuring eyesight corresponding to a predetermined eyesight value is projected on the fundus Ef. This process is performed by the controller 210. This predetermined eyesight value is a preliminarily set eyesight value such as an eyesight value considered as having good eyesight (for example, 1.0). The subject inputs the response content against this visual target for measuring eyesight using the input device 300.

The controller 210 determines whether the input response content is true or false. This process is executed by, for example, judging whether or not the direction indicated by the input device 300 matches the direction of the rift in the Landolt ring displayed on the LCD 39 as a visual target for measuring eyesight, and determining it as a correct answer if they match or determining it as a wrong answer if they do not match.

If the response content is determined as a correct answer, the controller 210 controls the scan drive 70 to change the direction of the Galvano mirrors 43, 44 and scans the scanning region superposed on the projection region of said visual target for measuring eyesight on the fundus Ef with the signal light LS.

The CCD image sensor 120 detects interference light LC of the signal light LS and the reference light LR. The image forming part 220 forms a tomographic image of the above-mentioned scanning region based on the detection results. When this scanning region is a two-dimensional region, the image forming part 220 forms a tomographic image on each of a plurality of cross sections (scanning lines) within this scanning region, and the image processor 230 forms a three-dimensional image of this scanning region based on these tomographic images. The main controller 211 stores the formed OCT image (tomographic image or three-dimensional image) and above-mentioned predetermined eyesight value in the storage 212 while correlating them to each other. At this time, information indicating the projection region of the visual target for measuring eyesight on the fundus Ef (for example, display position of the visual target for measuring eyesight on the LCD 39, position of the projection region on the fundus image, etc.) may be stored while being correlated with the OCT image and the predetermined eyesight value.

According to such a modification example, an OCT image of a site in the fundus Ef having at least the predetermined eyesight value can be automatically acquired.

As a further modification example, it is also possible to configure such that the OCT image of the measurement site can be acquired even when the eyesight value of the measurement site in the fundus Ef is below the predetermined value. As a specific example, if the response to the visual target for measuring eyesight of a predetermined eyesight value (for example, 1.0) is determined to be wrong, the controller 210 allows the visual target for measuring eyesight corresponding to the next lower eyesight value (for example, 0.8) to be displayed on the LCD 39. Then, if a correct answer is obtained for this visual target for measuring eyesight projected on the fundus Ef, the controller 210 controls the scan drive 70 to change the direction of the Galvano mirrors 43, 44 and scan the scanning region superposed on the projection region of this visual target for measuring eyesight on the fundus Ef with the signal light LS. The image forming part 220 etc. forms an OCT image based on the detection results of interference light LC of the signal light LS and the reference light LR. The main controller 211 stores the formed OCT image and above-mentioned eyesight value in storage 212 while correlating them to each other. At this time, information indicating the projection region of the visual target for measuring eyesight on the fundus Ef may be stored while being correlated to the OCT image and the eyesight value.

It should be noted that, if a wrong answer is obtained again, the visual target for measuring eyesight corresponding to still lower eyesight values may be used to conduct the examination. Moreover, it is also possible to preset the lowest eyesight value for conducting the eyesight measurement.

In the above embodiment, the position of the reference mirror 114 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 2 and the OCT unit 100 with respect to the eye E to change the optical path length of the signal light LS. Moreover, in a case that an object is not a living site or the like, it is also effective to change the optical path length difference by moving the object in the depth direction (z-direction).

The computer program used in the above embodiments can be stored in any kind of recording medium that can be read by a drive device of a computer. As this recording medium, for example, an optical disk, a magneto-optic disk (CD-ROM, DVD-RAM, DVD-ROM, MO, and so on), and a magnetic storage (a hard disk, a Floppy Disk™), ZIP, and so on) can be used. Moreover, it is possible to store into a storing device such as a hard disk drive and a memory. Besides, it is possible to transmit/receive this program through a network such as internet or LAN etc.

What is claimed is:

1. A fundus observation apparatus comprising:
   a projection part that includes a display part to display a visual target for measuring vision, and projects, via a predetermined optical path, said displayed visual target for measuring vision to the fundus of an eye;
   a light source that outputs low-coherence light;
   an optical system that splits said output low-coherence light into signal light and reference light, generates interference light by superposing said signal light that has passed through said fundus via said predetermined optical path and said reference light that has passed through a reference optical path, and detects said interference light;
   a scanning part that scans said fundus with said signal light;
   a controlling part that overlaps the projection region of said visual target for measuring vision projected by said projection part and the scanning region of said signal light scanned by said scanning part each other;
   an image forming part that forms an image of said fundus based on the detection results of interference light generated by superposing said signal light with which said scanning region is scanned and said reference light; and
   a storage part that stores said formed image and a vision value measured using said visual target for measuring vision while correlating them with each other.

2. The fundus observation apparatus according to claim 1, wherein said controlling part controls said projection part based on the scanning region of said signal light scanned by said scanning part to overlap the projection region of said visual target for measuring vision in said fundus on the scanning region of said signal light.

3. The fundus observation apparatus according to claim 2, wherein:
   said display part displays a fixation target for fixing said eye along with said visual target for measuring vision;
   said projection part projects said displayed fixation target on said fundus along with said visual target for measuring vision; and
   said controlling part changes said projection region by changing, based on said scanning region, the relative display positions of said visual target for measuring vision and said fixation target displayed by said display part.

4. The fundus observation apparatus according to claim 1, wherein said controlling part controls said scanning part based on the display position of said visual target for measuring vision displayed by said display part to overlap the scanning region of said signal light in said fundus on the projection region of said visual target for measuring vision.

5. The fundus observation apparatus according to claim 1, wherein said controlling part allows said visual target for measuring vision corresponding to different vision values to be projected on said fundus, by allowing said visual target for measuring vision of different sizes to be displayed on said display part to change the size of said projection region.

6. The fundus observation apparatus according to claim 5, wherein:
   said predetermined optical path is provided with a focusing lens that moves along an optical axis thereof to change the focus position of light towards said fundus; and
   said controlling part adjusts the size of said visual target for measuring vision displayed on said display part based on the position of said focusing lens.

7. The fundus observation apparatus according to claim 5, further comprising an operation part for inputting response contents for said visual target for measuring vision projected on said fundus, wherein
   said controlling part changes the size of said visual target for measuring vision displayed on said display part based on said input response contents, and determines the vision value of said eye based on said response contents according to this change.

8. The fundus observation apparatus according to claim 1, further comprising an operation part for inputting response contents for said visual target for measuring vision projected on said fundus, wherein said controlling part controls said projection part to project said visual target for measuring vision corresponding to a predetermined vision value to said fundus, determines whether said input response contents for this visual target for measuring vision are true or false, and if it is determined that they are correct, then controls said scanning part to scan said scanning region overlapping the projection region with said signal light.

9. The fundus observation apparatus according to claim 1, wherein said light source outputs invisible light as said low-coherence light.

10. The fundus observation apparatus according to claim 9, wherein said light source outputs near-infrared light of center wavelength within the range substantially from 1050 to 1060 nm.

* * * * *